(12) United States Patent
Suzuki et al.

(10) Patent No.: US 8,755,103 B2
(45) Date of Patent: Jun. 17, 2014

(54) PLASMA SHUTTER FORMING APPARATUS AND FORMING METHOD

(75) Inventors: Masayuki Suzuki, Kizukawa (JP); Hiromitsu Kiriyama, Kizukawa (JP); Izuru Daito, Kizukawa (JP); Hajime Okada, Kizukawa (JP); Hironori Sugiyama, Kizukawa (JP); Shinichi Matsuoka, Hamamatsu (JP); Hirofumi Kan, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 458 days.

(21) Appl. No.: 12/910,089

(22) Filed: Oct. 22, 2010

(65) Prior Publication Data

US 2011/0096385 A1 Apr. 28, 2011

(30) Foreign Application Priority Data

Oct. 23, 2009 (JP) ................................. 2009-244896

(51) Int. Cl.
*G02B 26/04* (2006.01)

(52) U.S. Cl.
USPC .......................................... 359/228; 359/297

(58) Field of Classification Search
USPC ................. 359/227–236, 297; 372/9–33, 109
See application file for complete search history.

(56) References Cited

U.S. PATENT DOCUMENTS 4,194,813 A * 3/1980 Benjamin et al. ............. 359/297
4,257,017 A * 3/1981 Bradley et al. ................ 359/297

FOREIGN PATENT DOCUMENTS

JP 2008-22994 2/2008

* cited by examiner

*Primary Examiner* — Stephone B Allen
*Assistant Examiner* — James McGee
(74) *Attorney, Agent, or Firm* — Wenderoth, Lind & Ponack, L.L.P.

(57) ABSTRACT

A plasma shutter forming apparatus for forming a plasma shutter used in a system configured to generate and accelerate radiations by irradiating a target with a laser pulse and generating a high-density plasma for blocking the laser pulse which is returned as a feedback light to upstream of the system without being absorbed by the high-density plasma, including a plasma shutter generating target, and a plasma shutter triggering laser irradiator, wherein the laser pulse from the plasma shutter triggering laser irradiator is directed to the plasma shutter generating target to generate the high-density plasma and form the plasma shutter, thereby blocking the laser pulse which is returned as the feedback light. Optics are prevented from becoming damaged by feedback light reflecting when generating the high-density plasma in a laser-driven radiation generating system and returning back to the upstream of the laser system.

4 Claims, 4 Drawing Sheets

PLASMA SHUTTER FORMING APPARATUS AND FORMING METHOD

BACKGROUND OF THE INVENTION

I. Technical Field

The present invention relates to an apparatus for forming a plasma shutter configured to effectively block laser pulses returned as feedback light when generating radiations such as particle beams (proton, ion, etc.), X-rays, terahertz waves by irradiating a target with the laser pulses, and a method of the same.

II. Description of the Related Art

In recent years, advances have been made along diagnosis and medical treatment technology achieved by generating particle beams, such as proton beams or carbon-ion-beams, by irradiating a target with a laser beam, and then irradiating diseased parts of human bodies with the generated particle beams. The applicants of the invention have proposed a particle beam therapeutic device which achieves improved medical treatment and diagnosis with feedback from a radiologist reflected thereto in real time on the same floor in JP-A-2008-22994.

This particle beam therapeutic device is capable of exceedingly downsizing a particle beam generator to allow the same to be installed and used on the same floor as a diagnosis support devices (PET, X-ray CT and MRI, and ultrasonic therapy apparatus), and hence may be installed directly in a medical site and used for diagnoses and medical practices. FIG. 4 schematically shows an example of configuration of the particle beam generator in the particle beam therapeutic device.

A proton beam generating mechanism shown in FIG. 4 includes a laser device 21 configured to generate a laser beam 25 for obtaining a required proton beam, a laser beam transmitting device 22 configured to transmit the generated laser beam 25 via optical components such as a plurality of lenses and mirrors, a laser beam focusing part 23 configured to focus the transmitted laser beam 25 to a proton beam generating target, and a proton beam generating unit 24 configured to irradiate a target with the laser beam 25 focused by the laser beam focusing part 23 and generate a desired proton beam 26 from the target.

This example describes detailed configurations from the laser device 21 to the proton beam generating unit 24 which constitute the proton beam generating mechanism and, more specifically, a portion of the proton beam generating unit 24 which irradiates a thin tape target, which is the proton beam generating target, with the laser beam 25 to generate the proton beam 26 in detail.

The dimension of a focusing mirror 23a which constitutes the laser beam focusing part 23 is on the order of 200 mm, which is a dimension convenient for realizing an exceedingly compact proton beam generating mechanism. Specifically, in order to realize the downsizing, a thin film tape target 24a is employed in the proton beam generating unit 24, and the proton beam 26 is generated by irradiating the thin film tape target 24a as the proton beam generating target with the laser beam 25. The thin film tape target 24a, being wound around a tape supply reel 24b, is configured to be transferred by being taken up by a tape winding reel 24c, and a laser beam irradiation position is set by two rotating rolls 24d provided in abutment thereto so as to interpose the laser beam irradiation position between them.

In the configuration as described above, the laser device 21 generates the laser beam 25 having a required power and a beam diameter. The generated laser beam 25 is directed toward the thin film tape target 24a and focused on a tape target irradiation position P thereof through the laser beam transmitting device 22 and the laser beam focusing part 23. Irradiation of the laser beam 25 generates plasma. In this case, approximately 50% the laser beam 25 is absorbed by the plasma, and the remaining part of the laser beam 25 returns back to the upstream side of a laser system as feedback light.

In contrast, recently, development of proton beams generating laser for a compact laser-driven proton beam generating device for medical use is in progress. In order to do so, laser pulses having high peak intensity of energy are required. In order to obtain such laser pulses, a chirp pulse amplification (hereinafter referred to as CPA) technique is employed. FIG. 5 is a drawing schematically showing a configuration of a laser-driven proton beam generating device using the CPA technique in the related art. The CPA technique is also applicable to the device shown in FIG. 4.

In FIG. 5, reference numeral 1 designates a space having a pressure not higher than 1 Pa. Reference numeral 1' designates a space having a pressure higher than 1 Pa and includes atmospheric pressure. Reference numeral 2 designates a proton beam generating target, which is a target for generating and accelerating the proton beam, reference numeral 3 designates a laser producing plasma, reference numeral 4 designates feedback light, reference numeral 5 designates a proton beam generating laser pulse, reference numeral 6 designates a focusing optics formed of a mirror or a lens, reference numeral 7 designates an optics formed of a polarizing plate or the like, reference numeral 8 designates a pulse compressor including a diffraction grating and a laser reflecting optics, and reference numeral 9 designates a laser-transmitting optics.

The proton beam generating laser pulse 5 emitted from a laser pulse generating device, not shown, enters a high-vacuum portion 1 from the laser-transmitting optics 9, passes through an optical system made up of the pulse compressor 8 including the diffraction grating and the laser reflecting optics, the optics 7, and the focusing optics 6, and is focused on the proton beam generating target 2. When the proton beam generating laser pulse 5 is focused on the proton beam generating target 2, the laser producing plasma 3 at a high density is generated. At this time, 50% the proton beam generating laser pulse 5 is absorbed by the laser producing plasma 3, and the remaining laser pulse returns back to the upstream of the laser system (from the pulse compressor including the diffraction grating and the laser reflecting optics to an oscillator) as the feedback light 4.

As described above, in the laser-driven particle beam generating device in the related art, proton and ion are generated and accelerated to be used in medical treatment and diagnosis. However, in the device in the related art of this type, the optics may be damaged due to the feedback light returned back to the upstream of the laser system when the plasma is generated. In particular, in the laser system employing CPA method, a problem of damages of the diffracting grating and the laser reflecting optics in the pulse compressor is serious.

Therefore, in the related art, methods using an optics, in which polarization of light such as Faraday isolator or Pockels cell is used, are employed as a countermeasure for the feedback light.

However, the optics such as the Faraday isolator or the Pockels cell are difficult to upsize. Therefore, it is difficult to install these optics immediately after the pulse compressor including the diffraction grating and the laser reflecting optics which enlarge the beam diameter of the laser pulse. It is difficult to install the Faraday isolator in terms of elongation of the pulse width when a damage threshold value and the CPA method are employed. In addition, since the Pockels cell is triggered by an electric signal, the required rise time is about 50 ps at the shortest. Therefore, it cannot block the feedback light satisfactorily.

SUMMARY OF THE INVENTION

In view of such circumstances in the related art, it is an object of the invention to prevent optics from becoming damaged by feedback light reflecting when generating high-density plasma in a laser-driven radiation generating system and returning back to the upstream of the laser system.

In order to solve the above described problems, according to the first aspect of the invention, there is provided a plasma shutter forming apparatus configured to form a plasma shutter used in a system configured to generate and accelerate radiations by irradiating a target with a laser pulse and generating a high-density plasma for blocking the laser pulse which is returned as a feedback light to upstream of the system without being absorbed by the high-density plasma including: a plasma shutter generating target arranged for forming the plasma shutter, and a plasma shutter triggering laser irradiator configured to irradiate the plasma shutter generating target with the laser pulse, wherein the laser pulse from the plasma shutter triggering laser irradiator is directed to the plasma shutter generating target to generate the high-density plasma and form the plasma shutter, thereby blocking the laser pulse which is returned as the feedback light.

According to the second aspect of the invention, there is provided a plasma shutter forming apparatus wherein the density of the high-density plasma which forms the plasma shutter is in a range from $10^{17}$ to $10^{23}$ $cm^{-3}$.

According to the third aspect of the invention, there is provided a plasma shutter forming method for forming a plasma shutter used in a system configured to generate and accelerate radiations by irradiating a target with a laser pulse and generating a high-density plasma for blocking the laser pulse which is returned as a feedback light to upstream of the system without being absorbed by the high-density plasma including: forming the plasma shutter by irradiating a plasma shutter generating target with a plasma shutter triggering laser pulse to generate the high-density plasma and blocking the laser pulse returned as the feedback light.

According to the fourth aspect of the invention, there is provided the method as described in the third aspect of the invention, characterized in that the density of the high-density plasma which forms the plasma shutter is in a range from $10^{17}$ to $10^{23}$ $cm^{-3}$ is provided.

According to the invention, with the employment of the configuration and the method as described above, the feedback light returning back to the upstream of the laser system by being reflected when generating the high-density plasma in a laser-driven radiation generating system is blocked by being absorbed and reflected by the plasma shutter. Accordingly, the optics are prevented from becoming damaged by the feedback light.

The radiations here include, for example, particle beams, X-rays, and terahertz waves. The particle beams include, for example, ion beams such as proton beams or carbon-ion-beams, neutron beams, and electron beams. The X-rays have wavelengths in a range from 0.01 to 150 nm, and the terahertz waves are electromagnetic waves having a wavelength of at least 1 μm.

DETAILED DESCRIPTION OF THE PREFERRED EMBODIMENT

The invention will be described in detail below.

The invention relates to a device for forming a plasma shutter used in a laser-driven radiation generating system configured to generate radiations by irradiating a target with a laser pulse and generating a high-density plasma, the device blocking the laser pulse which is returned as a feedback light to upstream of the system without being absorbed by the high-density plasma, including a plasma shutter generating target arranged for forming the plasma shutter, and a plasma shutter triggering laser irradiator configured to irradiate the plasma shutter generating target with the laser pulse, wherein the laser pulse from the plasma shutter triggering laser irradiator is directed to the plasma shutter generating target to generate the high-density plasma and form the plasma shutter, thereby blocking the laser pulse which is returned as the feedback light.

Figure 1:
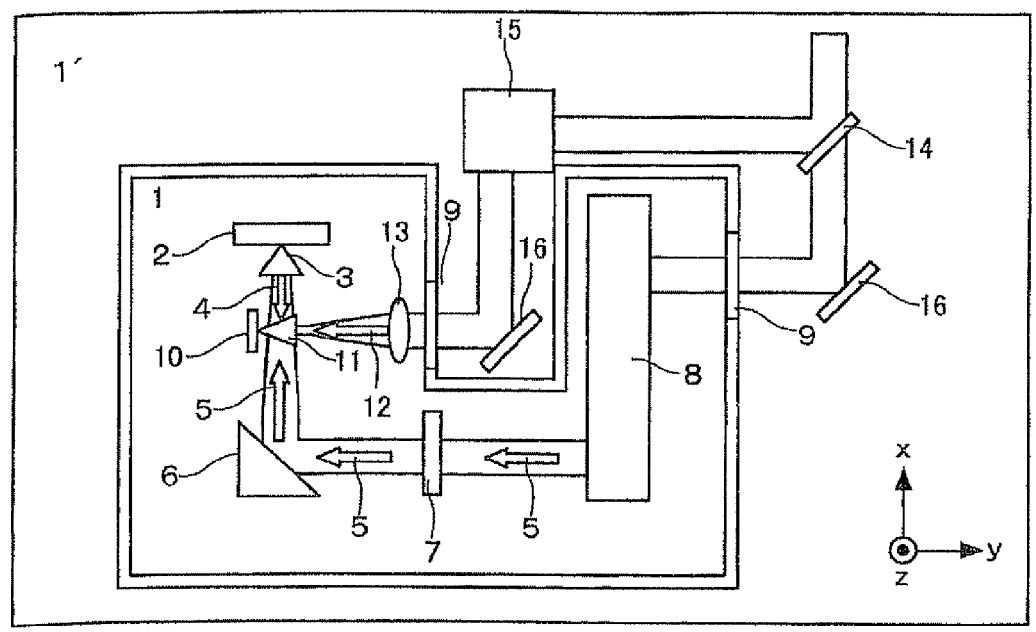
FIG. 1 is a drawing schematically showing a configuration of a laser-driven proton beam generating system having a plasma shutter forming apparatus according to an embodiment of the invention.
Figure 5:
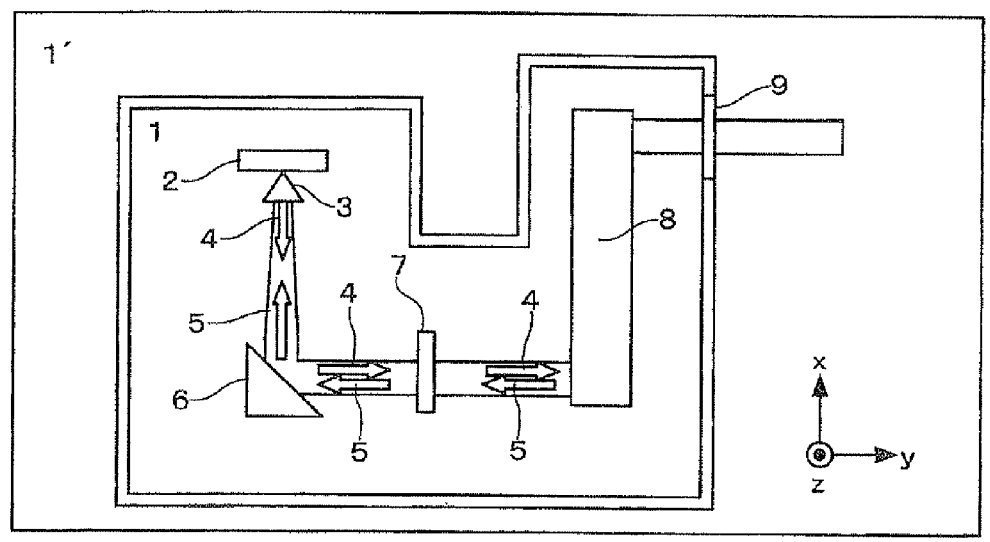
FIG. 5 is a drawing schematically showing a configuration of a laser-driven proton beam generating device using a CPA technique in the related art.

FIG. 1 is a drawing schematically showing a configuration of a laser-driven proton beam generating system having a plasma shutter forming apparatus according to an embodiment of the invention. In FIG. 1, the same elements as in FIG. 5 are designated by the same reference numerals.

Figure 4:
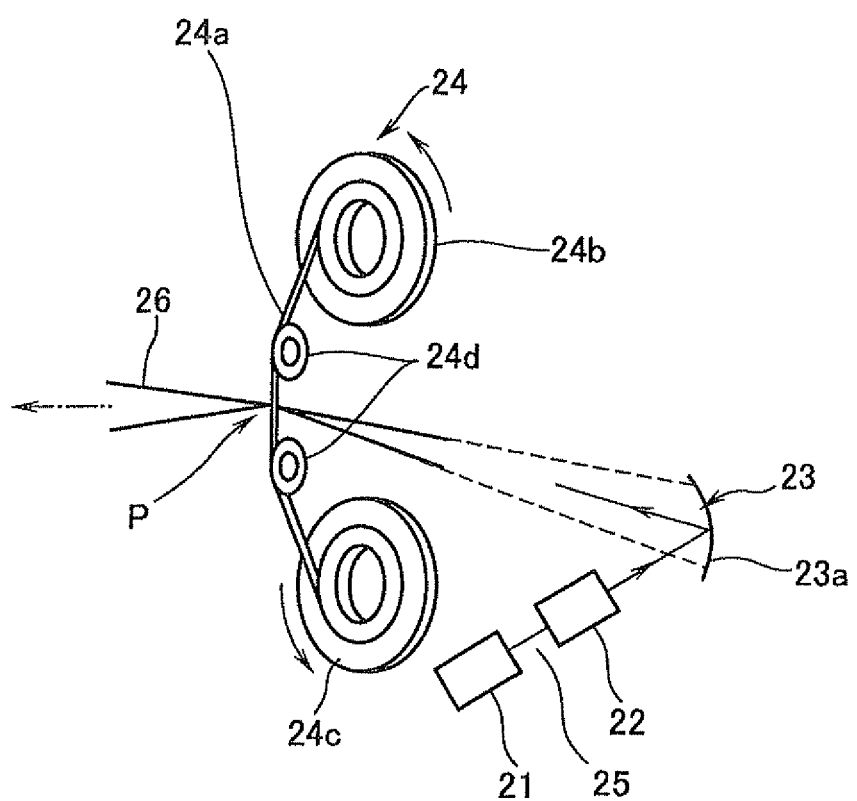
FIG. 4 is a drawing schematically showing a configuration of a proton beam generating mechanism in a particle beam therapeutic device in the related art.

A proton beam generating target 2 generates a laser producing plasma 3, and generates and accelerates protons, and typically a solid state target is used. For example, Al, Cu, C, Ti, W, polyethylene-based polymer material or the like are preferably used. These elements are preferable because they can be used in the form of the tape as described in conjunction with the apparatus shown in FIG. 4. As other choices, substances which can be kept in a solid state in room temperatures other than alkali metals, alkali-earth metals and radioactive materials can be employed. However, Cd, As, Te and Tl being highly toxic are preferably avoided. Cryogenic Target which can be generated by cooling inert gas (JP-A-2003-303696 (Japanese Patent No. 3759089)) can also be used. When using the gas target, a nozzle formed of a thin tube applied with a back pressure is used. In addition, a liquid drop target (JP-A-2004-235158 (Japanese Patent No. 3943089)) or Cluster Target may also be used.

The laser producing plasma 3 is a high-density plasma generated on the surface of the proton beam generating target 2 when being irradiated with the proton beam generating laser pulse 5. The laser producing plasma 3 exists for a period of the pulse width of a proton beam generating laser pulse 5, and the duration thereof depends on the time width of the proton beam generating laser pulse 5. The growing time is approximately 1 ps, which means that the laser producing plasma 3 grows very quickly. The density of the laser producing plasma 3 is on the order of $10^{17}$ to $10^{23}$ $cm^{-3}$. The laser pulse which is not absorbed when the laser producing plasma 3 is generated is on the order of 50%, and the laser pulse which is not absorbed is reflected as a feedback light 4.

The proton beam generating laser pulse 5 is emitted from a laser device, not shown, and is subjected to CPA amplification in the optical system of the present embodiment. The intensity of the proton beam generating laser pulse 5 directed onto the proton beam generating target 2 is on the order of $10^{15}$ to $10^{23}$ $Wcm^{-2}$, the energy is on the order of 0.01 to 10 J/pulse, the pulse width is on the order of 10 fs to 20 ns, and the repetition is on the order of 0.1 to 1000 Hz. The lasers which can be used here is lasers which can be amplified by CPA amplification, and includes Ytterbium-doped YAG (Yb:YAG) laser, Titanium doped sapphire (Ti:sapphire) laser, Neodymium glass (Nd:glass) laser, Krypton Fluoride (KrF) laser, and dye laser, and Neodymium-doped YAG (Nd:YAG) laser or carbon dioxide ($CO_2$) laser may also be used depending on the cases.

A focusing optics 6 is configured to focus the proton beam generating laser pulse 5 onto an irradiation point on the proton beam generating target 2, and may be a mirror or a lens.

An optics 7 is used for polarizing the proton beam generating laser pulse 5, and a pulse compressor 8 including a diffraction grating and a laser-reflecting optics is used for compressing pulses during the CPA amplification. A laser-transmitting optics 9 is used for causing the proton beam generating laser pulse 5 to enter. A laser-reflecting optics 16 on the right side has a role to change the direction of the optical path of the proton beam generating laser pulse 5.

A plasma shutter generating target 10 is an element which constitutes the plasma shutter forming apparatus, and is for forming a plasma shutter 11 formed of high-density plasma. The material of the target may be similar material as that used for the proton beam generating target 2. The plasma shutter generating target 10 may be installed at arbitrary positions between the proton beam generating target 2 and the focusing optics 6, and is installed at a position which allows the high-density plasma to block the optical path of the proton beam generating laser. As shown in FIG. 1, the plasma shutter generating target 10 can be installed at arbitrary positions where the plasma shutter triggering laser reaches after having proceeded toward the direction of irradiation of the proton beam generating laser and straddled the proton beam generating laser. The positions of installation may be one position or a plurality of positions. It may be installed between the focusing optics 6 and the pulse compressor 8 including the diffraction grating and the laser-reflecting optics. For example, dimensions of the plasma shutter generating target 10 are 1 cm×1 cm, and at least 100 nm in thickness. However, the dimensions do not necessarily have to be those shown above as long as it can block the feedback light 4.

Figure 2:
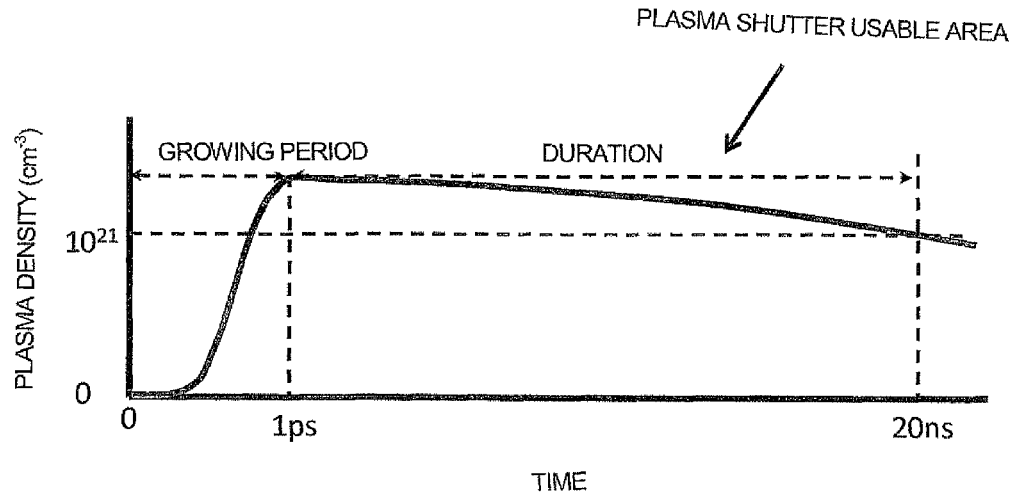
FIG. 2 is a graph showing an example of a relationship between a growing period and duration of a laser producing plasma and plasma shutter usable area.

The plasma shutter 11 is a high-density plasma generated on the plasma shutter generating target 10 when irradiating the same with a plasma shutter triggering laser pulse 12. The high-density plasma which constitutes the plasma shutter 11 exists for a period of the pulse width of a plasma shutter triggering laser pulse 12 in the same manner as the laser producing plasma 3, and the duration thereof depends on the time width of the plasma shutter triggering laser pulse 12. The growing time is approximately 1 ps, which means that it grows very quickly. The density of the plasma can be controlled between the $10^{17}$ to $10^{23}$ $cm^{-3}$, and the plasma density can be measured by a shift of diffraction fringes using an interferometer on the basis of laser beams. The plasma in this density area can block the feedback light 4 by absorbing the same sufficiently. FIG. 2 shows an example of a relationship between a growing period and duration of the plasma shutter 11 and a plasma shutter usable area. After the plasma shutter 11 has grown in a period on the order of 1 ps and assumed a density which can block the feedback light 4, it continues for a period on the order of 20 ns.

Branched part of a laser pulse emitted from the above-described laser device, not shown, may be used as the plasma shutter triggering laser pulse 12. The plasma shutter triggering laser pulse 12 is focused by a plasma shutter forming focusing optics 13 including lens and the like, and is directed on the plasma shutter generating target 10. In this case, it is preferable to retrieve and use part of the laser pulse immediately before the pulse compression using the pulse compressor 8 including the diffraction grating and the laser-reflecting optics in the chirp pulse amplification (CPA) laser system. The plasma shutter triggering laser pulse 12 which can be used here is the one having the intensity of irradiation of about $10^9$ to $10^{23}$ $Wcm^{-2}$, energy of at least 0.1 mJ/pulse, and a pulse width of at least 10 fs. The value of repetition may be any value as long as it is the same as that of the proton beam generating laser pulse 5. The diameter of the focused laser beam of the plasma shutter triggering laser pulse 12 may be on the order of 10 to 500 μm in the case of the point focusing, and on the order of 20 μm in width and 0.5 to 3 mm in length in the case of the linear focusing. However, the diameter is not limited to these dimensions as long as the feedback light 4 is blocked sufficiently.

Figure 3:
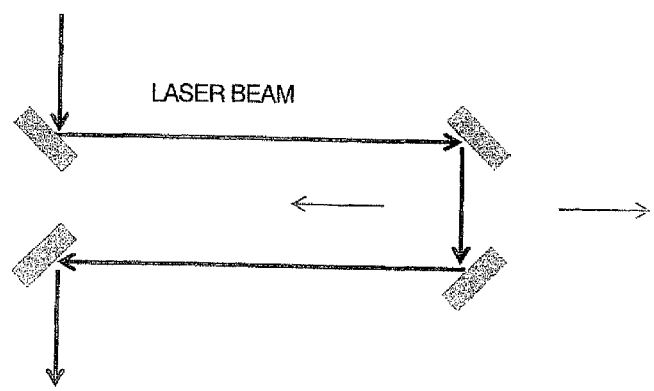
FIG. 3 is a drawing schematically showing an example of an optical delay element.

In order to use part of the laser beam emitted from the above-described laser device, not shown, as the plasma shutter triggering laser pulse 12, the laser beam is divided by a laser beam splitting optics (beam splitter) 14, is optically delayed by an optical delay element 15 for adjustment of the timing with the proton beam generating laser pulse 5, then is changed in direction of the optical path by the laser-reflecting optics 16 made up of a mirror or the like, and is guided to the plasma shutter focusing optics 13. An example of the optical delay element 15 is schematically shown in FIG. 3. In this example, a mirror is installed on a stage, and the stage is moved in the direction indicated by arrows on a rail to differentiate the length of the optical path, thereby changing the time of arrival of the plasma shutter triggering laser pulse 12. A prism or the like may be used instead of the mirror.

If the plasma shutter triggering laser pulse 12 is capable of operating a separate laser system synchronously with a temporal jitter on the order of 0.5 ns, it can also be employed. In other words, an electric signal is generated by detecting a laser beam from an oscillator in the CPA laser system, for example, by a high-speed photodiode. Then part of the generated signal is divided. Subsequently, the divided signal is used to operate the plasma shutter triggering laser by an external trigger. The conditions of the laser energy, the concentration intensity, and the pulse width are the same as those when retrieving part of the laser pulse as described above.

The plasma shutter 11 does not interfere with the optical path of the proton beam generating laser pulse 5 when being directed on the proton beam generating target 2. When the proton beam generating laser pulse 5 reaches the proton beam generating target 2, the plasma shutter triggering laser pulse 12 is directed on the plasma shutter generating target 10, so that the high-density plasma is generated, and the plasma shutter 11 is formed. The time difference from the moment when the proton beam generating laser pulse 5 is focused on the proton beam generating target 2 and the plasma is generated to a moment when the plasma shutter triggering laser pulse 12 is focused on the plasma shutter generating target 10 falls within a time range on the order of −1 ns to 1 ns. If the feedback light can be prevented, the time range is not limited thereto.

Therefore, the plasma shutter 11 can effectively block the feedback light 4 due to the laser pulse which is not absorbed by the plasma generated when the proton beam generating laser pulse 5 is focused on the proton beam generating target 2. Accordingly, damages on the optics (the pulse compressor including the diffraction grating and the laser-reflecting optics, mirrors, wave plates, and so on) due to the feedback light 4 can be alleviated.

The invention claimed is:

1. A plasma shutter forming apparatus used in a system configured to generate a first high-density plasma by irradiating a plasma generating target with a first laser pulse and accelerate charged particles in the first high-density plasma, and the plasma shutter forming apparatus configured to generate a plasma shutter comprising a second high-density plasma for blocking the first laser pulse which is returned as a feedback light to upstream of the system without being absorbed by the first high-density plasma, the apparatus comprising:

a plasma shutter generating target arranged to form the plasma shutter between the plasma generating target and a focusing optics of the system;

a plasma shutter triggering laser irradiator configured to irradiate the plasma shutter generating target with a second laser pulse;

a laser beam splitting optics for dividing laser pulses emitted from a laser device into the first laser pulse to irradiate the plasma generating target and the second laser pulse to irradiate the plasma shutter generating target; and an optical delay element for adjusting of the timing of the second laser pulse with the first laser pulse, wherein the second laser pulse from the plasma shutter triggering laser irradiator is directed to the plasma shutter generating target to generate the second high-density plasma and form the plasma shutter, thereby blocking the first laser pulse which is returned as the feedback light.

2. The plasma shutter forming apparatus according to claim 1, wherein a density of the second high-density plasma which forms the plasma shutter is in a range from $10^{17}$ to $10^{23}$ cm$^{-3}$.

3. A plasma shutter forming method used in a system configured to generate a first high-density plasma by irradiating a plasma generating target with a first laser pulse and accelerate charged particles in the first high-density plasma, and the plasma shutter forming method being for generating a plasma shutter comprising a second high-density plasma for blocking the first laser pulse which is returned as a feedback light to upstream of the system without being absorbed by the first high-density plasma, the method comprising:

arranging a plasma shutter generating target to form the plasma shutter, between the plasma generating target and a focusing optics of the system;

dividing laser pulses emitted from a laser device, by a laser splitting optics, into the first laser pulse to irradiate the plasma generating target and a second laser pulse to irradiate the plasma shutter generating target;

adjusting the timing of the second laser pulse with the first laser pulse by an optical delay element; and irradiating the plasma shutter generating target with the second laser pulse to generate the second high-density plasma as the plasma shutter, thereby blocking the first laser pulse which is returned as the feedback light.

4. The plasma shutter forming method according to claim 3, wherein a density of the second high-density plasma forming the plasma shutter is in a range from $10^{17}$ to $10^{23}$ cm$^{-3}$.

* * * * *